(12) United States Patent
Tezuka et al.

(10) Patent No.: US 9,700,278 B2
(45) Date of Patent: Jul. 11, 2017

(54) RADIATION IMAGE CAPTURING SYSTEM

(71) Applicant: Konica Minolta, Inc., Chiyoda-ku, Tokyo (JP)

(72) Inventors: Hidetake Tezuka, Tachikawa (JP); Yuuichi Nishijima, Mitaka (JP); Akio Takagi, Hino (JP); Koji Takemura, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 10 days.

(21) Appl. No.: 14/808,461

(22) Filed: Jul. 24, 2015

(65) Prior Publication Data
US 2016/0022242 A1 Jan. 28, 2016

(30) Foreign Application Priority Data

Jul. 25, 2014 (JP) ................. 2014-151577

(51) Int. Cl.
*A61B 6/00* (2006.01)

(52) U.S. Cl.
CPC ............ *A61B 6/563* (2013.01); *A61B 6/4283* (2013.01); *A61B 6/4405* (2013.01); *A61B 6/4411* (2013.01); *A61B 6/467* (2013.01); *A61B 6/548* (2013.01); *A61B 6/4233* (2013.01)

(58) Field of Classification Search
CPC ....... A61B 6/563; A61B 6/4283; A61B 6/467; A61B 6/548; A61B 6/4411; A61B 6/4405; A61B 6/4233
USPC ...................................................... 250/393
See application file for complete search history.

(56) References Cited

U.S. PATENT DOCUMENTS

2006/0094364 A1 5/2006 Hirota et al.
2010/0202589 A1 8/2010 Ohta et al.

FOREIGN PATENT DOCUMENTS

| JP | 2010158454 | * | 7/2010 | ............... A61B 6/00 |
| JP | 2010158454 A | | 7/2010 | |
| JP | 2014094306 A | | 5/2014 | |

OTHER PUBLICATIONS

Extended European Search Report corresponding to Application No. 15176454.5-1854; Date of Mailing: Dec. 21, 2015.

* cited by examiner

*Primary Examiner* — David Porta
*Assistant Examiner* — Gisselle Gutierrez
(74) *Attorney, Agent, or Firm* — Cantor Colburn LLP

(57) ABSTRACT

Disclosed is a radiation image capturing system including a portable radiation image capturing apparatus and a portable console. The portable radiation image capturing apparatus can generate image data according to irradiated radiation and transmit the generated image data by wireless communication. The portable console includes a first wireless communication unit which can receive the image data transmitted from the radiation image capturing apparatus and a second wireless communication unit which can communicate with an external apparatus or system by wireless communication. The console gives priority to one wireless communication than the other between the wireless communication through the first wireless communication unit or the wireless communication through the second wireless communication unit.

7 Claims, 8 Drawing Sheets

| CAPTURING ORDER ID | PATIENT ID | PATIENT NAME | SEX | AGE | MEDICAL DEPARTMENT | CAPTURING SITE | CAPTURING DIRECTION |
|---|---|---|---|---|---|---|---|
| 001 | 100085 | M | MALE | 25 | ORTHOPEDICS | CHEST | FRONT P → A |
| 002 | 100085 | M | MALE | 25 | ORTHOPEDICS | STOMACH | FRONT P → A |
| 003 | 100085 | M | MALE | 25 | ORTHOPEDICS | HEAD | FRONT P → A |
| 004 | 100085 | M | MALE | 25 | ORTHOPEDICS | LEG | R |
| 005 | 100063 | W | FEMALE | 32 | SURGERY | CHEST | SIDE R → L |
| 006 | 100063 | W | FEMALE | 32 | SURGERY | STOMACH | FRONT A → P |

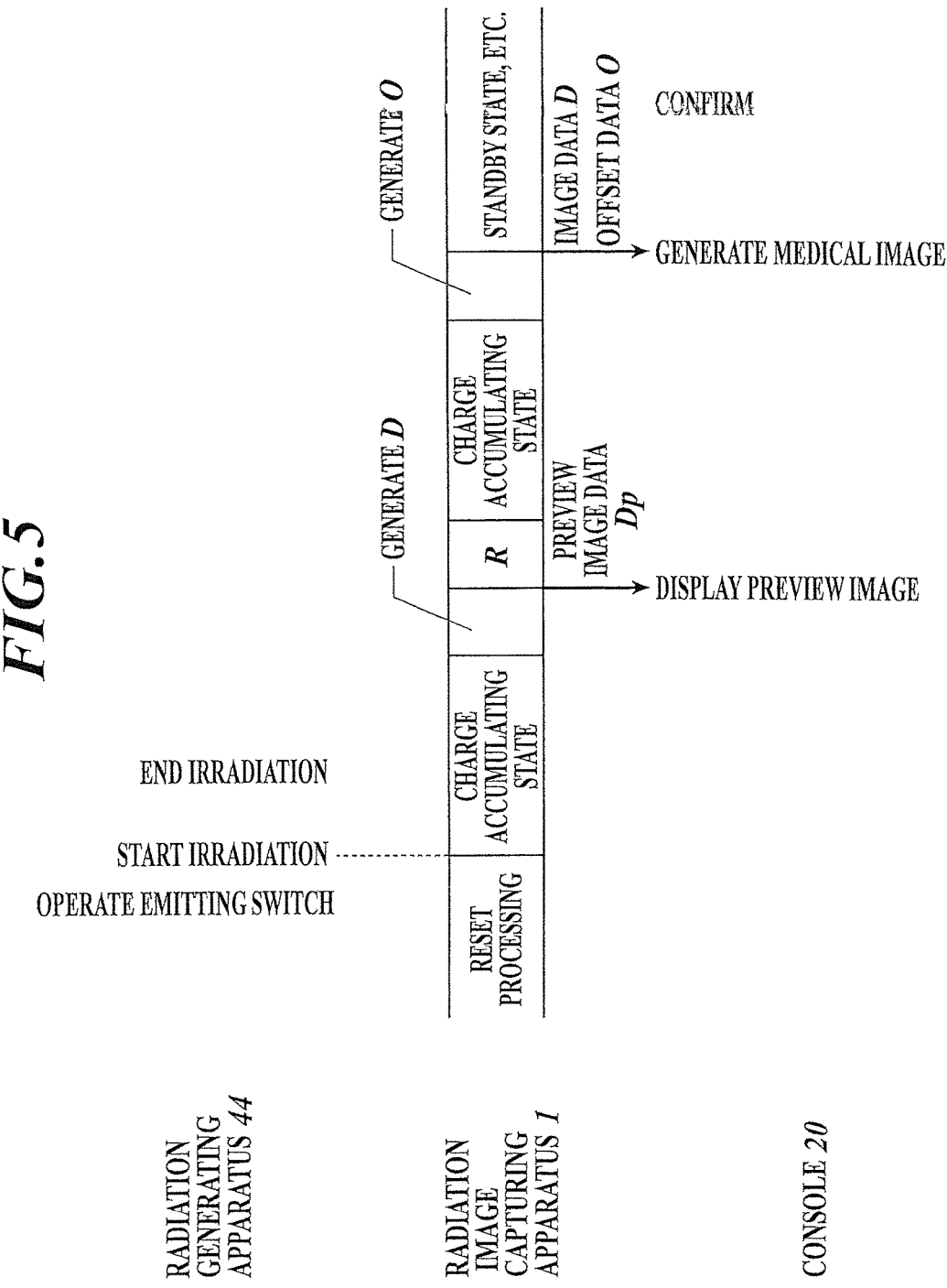

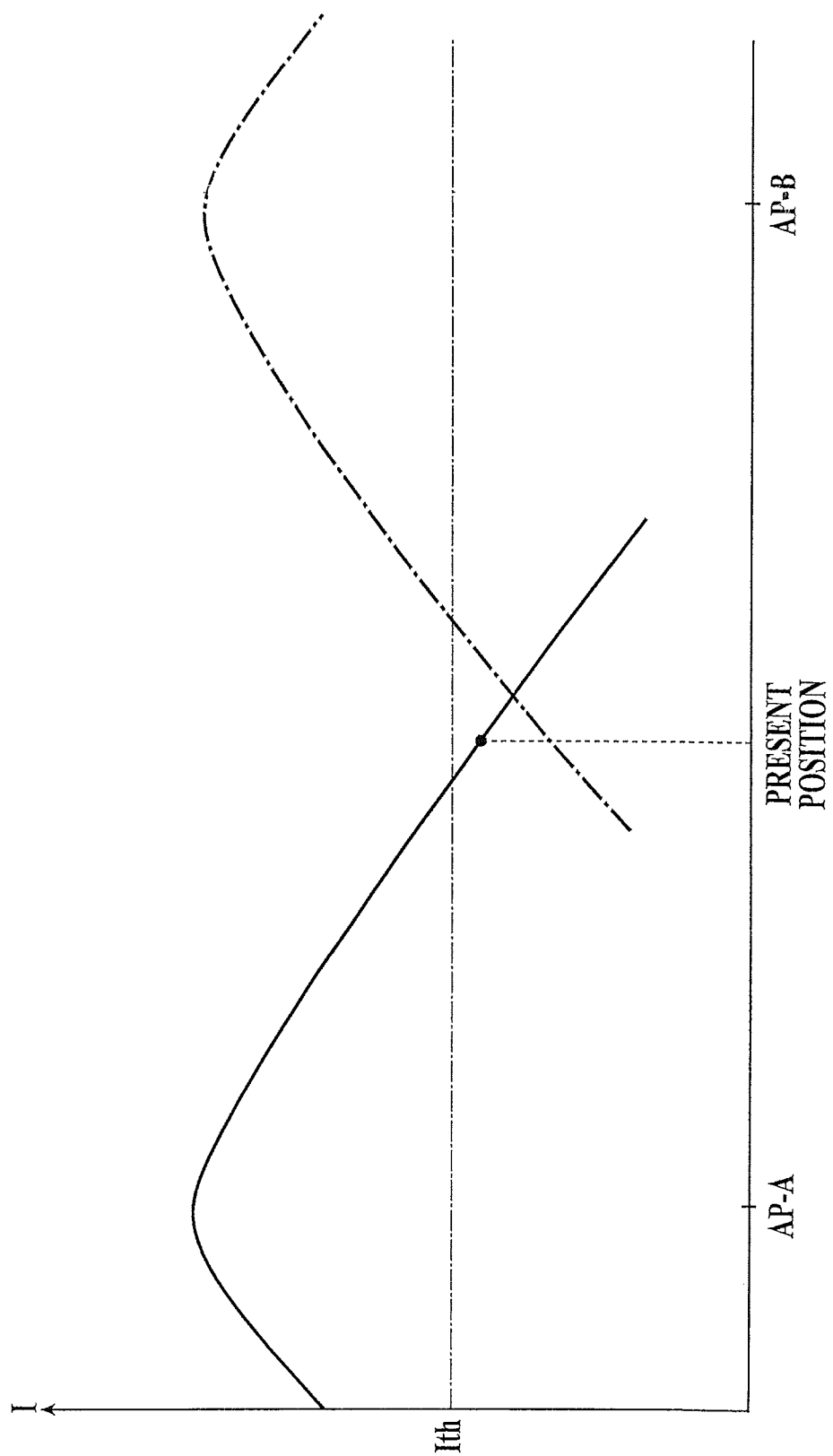

RADIATION IMAGE CAPTURING SYSTEM

CROSS REFERENCE TO RELATED APPLICATIONS

The present invention claims priority under 35 U.S.C. §119 to Japanese Application No. 2014-151577 filed Jul. 25, 2014, the entire content of which is incorporated herein by reference.

BACKGROUND

Field of the Invention

The present invention relates to a radiation image capturing system. Specifically, the present invention relates to a radiation image capturing system in which the portable console performs wireless communication with the FPD cassette, external system, etc.

Description of Related Art

In the field of radiation capturing, the method of capturing is shifting from analog to digital, specifically, the method of capturing is shifting from a conventional silver halide photography type using screen/film to photography using a CR (computed radiography) cassette with a stimulable phosphor sheet. Lately, various radiation image capturing apparatuses (Flat Panel Detector:FPD) are being developed. In such apparatuses, radiation is irradiated from a radiation source, and image data is generated according to the radiation which passes through the subject. Such apparatuses are used in capturing images to be provided in diagnosis in medical scenes such as hospitals.

Then, the image data generated in the radiation image capturing apparatus is transferred to a console, image processing is performed on the image data in the console, and the radiation image, in other words, the image for diagnosis is generated. The generated image for diagnosis may be transmitted from the console to an external apparatus or system such as a host computer, or a QA (Quality Assurance) station, PACS (Picture Archiving and Communication System), or the like.

Alternatively, for example, the console may transmit and receive information, etc. wirelessly. Specifically, the console may wirelessly obtain later described capturing order information from external systems such as HIS (Hospital Information System) or RIS (Radiology Information System) in facilities such as hospitals.

When the communication between the console and the external apparatus is connected by a wired network, the communication between the radiation image capturing apparatus and the console and the communication between the console and the external apparatus, etc. do not interfere with each other. However, when both the communication between the radiation image capturing apparatus and the console and the communication between the console and the external apparatus are performed by a wireless method, the problem of the above communication interfering with each other may occur.

In order to prevent such system, Japanese Patent No. 5298865 describes changing the method of the wireless communication to prevent interference of communication. For example, one method of wireless communication can be wireless communication with UWB (Ultra Wide Band) communication and the other method of the wireless communication can be wireless LAN (Local Area Network) communication.

However, depending on the facility such as hospitals, it is not possible to set the method of communication between the radiation image capturing apparatus and the console different from the method of communication between the console and the external apparatus as described in Japanese Patent No. 5298865. There are many facilities in which only one wireless communication method, such as a wireless LAN communication method, can be used.

Such situation may also occur in a radiation image capturing system in which a radiation image generating apparatus, console, etc. are loaded on a diagnosis car as described in Japanese Patent Application Laid-Open Publication No. 2014-94306. Specifically, Japanese Patent Application Laid-Open Publication No. 2014-94306 describes an example in which communication between the console and the external apparatus or the system is performed in a wireless method, but since the console and the radiation image capturing apparatus are formed on the diagnosis car as one, the communication between the console and the radiation image capturing apparatus is performed in a wired method.

It is assumed that in a radiation image capturing system formed on such diagnosis car, for example, a commercially available portable computer is used as the console and portable devices are used as the radiation image capturing apparatus and the console so that the diagnosis car can function as a capturing room. With this, the mobility when the system is moved is enhanced.

In this case, not only the communication between the console and the external apparatus or system but also communication between the radiation image capturing apparatus and the console is performed using the wireless function of the commercially available computer. However, the communication between the radiation image capturing apparatus and the console and the communication between the console and the external apparatus or system are each performed with a wireless method. In such case, when the frequency band used by both wireless communication is close, interference may occur.

For example, when information such as a plurality of images for diagnosis are transmitted collectively from the console to the external device or system, the time necessary to transmit the images for diagnosis may become relatively long. In such situation, when image data is transmitted from the radiation image capturing apparatus to the console while the image for diagnosis is transmitted from the console to the external apparatus, etc., the wireless communication may interfere with each other.

For example, when the transmission of the image data from the radiation image capturing apparatus to the console interferes with the transmission of the information of the image for diagnosis from the console to the external apparatus or system, either the transmission of the image data from the radiation image capturing apparatus to the console or the transmission of the information of the image for diagnosis from the console to the external apparatus or system runs out of time and error occurs in communication. In this case, the user performs the operation to send the image data or the information again. However, if the user is not used to the operation, in the worst case, the image data or the information of the image for diagnosis may be lost.

When the image data or the information is lost, the capturing needs to be performed again. When capturing is performed again, the amount of irradiation on the patient increases. This increases the burden of the patient.

SUMMARY

The present invention has been made in consideration of the above problems, and one of the main objects is to provide a radiation image capturing system which can reliably prevent interference between transmission of image data by wireless communication from a radiation image capturing apparatus to a console and wireless communication between a console and an external apparatus or system.

In order to achieve at least one of the above-described objects, according to an aspect of the present invention, there is provided a radiation image capturing system including:

a portable radiation image capturing apparatus which can generate image data according to irradiated radiation and transmit the generated image data by wireless communication; and a portable console including a first wireless communication unit which can receive the image data transmitted from the radiation image capturing apparatus and a second wireless communication unit which can communicate with an external apparatus or system by wireless communication, wherein, the console gives priority to one wireless communication than the other between the wireless communication through the first wireless communication unit or the wireless communication through the second wireless communication unit.

According to another aspect of the present invention, there is provided a radiation image capturing system including:

a portable radiation image capturing apparatus which can generate image data according to irradiated radiation and transmit the generated image data by wireless communication; and a portable console including a first wireless communication unit which can receive the image data transmitted from the radiation image capturing apparatus and a second wireless communication unit which can communicate with an external apparatus or system by wireless communication, wherein, the console uses a channel which is same as a wireless communication channel used in a facility for both of the wireless communication through the first wireless communication unit and the wireless communication through the second wireless communication unit.

According to another aspect of the present invention, there is provided a radiation image capturing system including:

a portable radiation image capturing apparatus which can generate image data according to irradiated radiation and transmit the generated image data by wireless communication; and a portable console including a first wireless communication unit which can receive the image data transmitted from the radiation image capturing apparatus and a second wireless communication unit which can communicate with an external apparatus or system, wherein, the console performs wireless communication through the first wireless communication unit and the wireless communication through the second wireless communication unit so that a channel used in the wireless communication through the first wireless communication unit is at least 2 channels apart from a channel used in the wireless communication through the second wireless communication unit.

According to the radiation image capturing system of the present invention, it is possible to reliably prevent the transmission of the image data by wireless communication from the radiation image capturing apparatus to the console from interfering the wireless communication between the console and the external device or system.

BRIEF DESCRIPTION OF THE DRAWINGS

The present invention will become more fully understood from the detailed description given hereinbelow and the appended drawings, and thus are not intended to define the limits of the present invention, and wherein;

FIG. 5 is a diagram showing an example of a capturing sequence when capturing is performed in a non-linking format;

FIG. 9 is a graph showing a different example of a relation between radio wave intensity and threshold level of access points AP-A and AP-B in the present position of the console.

DETAILED DESCRIPTION OF PREFERRED EMBODIMENTS

The embodiment of the radiation image capturing system of the present invention is described with reference to the drawings.

[Total Configuration of Radiation Image Capturing System]

Figure 1A:
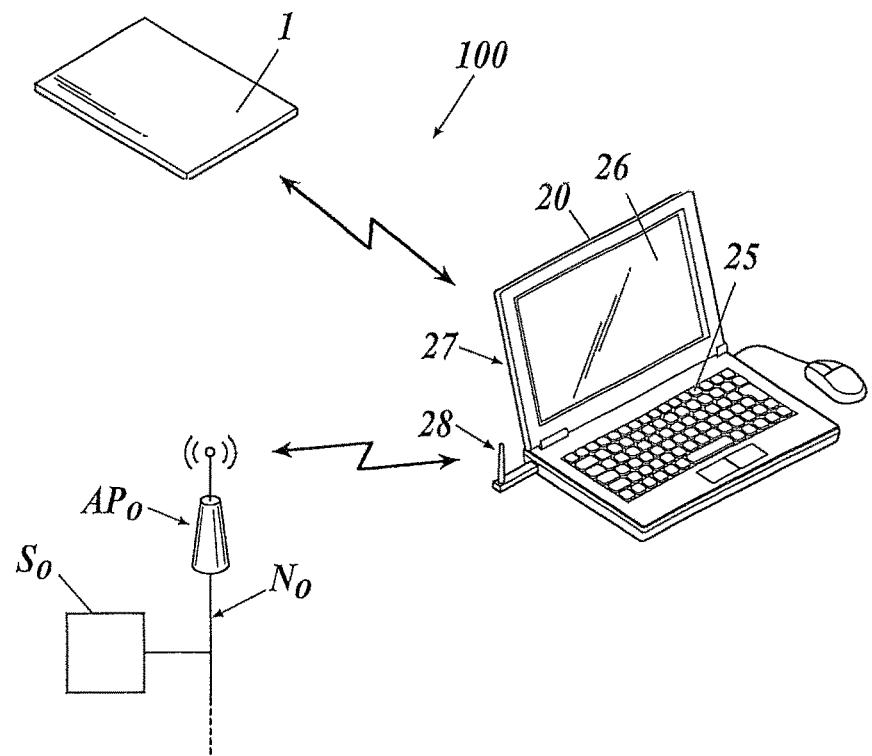
FIG. 1A is a conceptual diagram of a total radiation image capturing system of the present embodiment.

FIG. 1A is a conceptual diagram of a total radiation image capturing system of the present embodiment. According to the present embodiment, the radiation image capturing system 100 includes at least a portable radiation image capturing apparatus 1 and a console 20 consisting of a portable computer.

Although illustration is omitted, the radiation image capturing apparatus 1 is provided with radiation detecting elements arranged two dimensionally. The radiation detecting element generates charge according to the amount of radiation irradiated through the body of the patient which is the subject. The charge generated in each radiation detecting element is read out with a read out circuit to generate image data. The generated image data is stored in the storage unit in the radiation detecting element 1. The radiation image capturing apparatus 1 includes a wireless communication module provided with an antenna, etc. Each time capturing ends or after a string of plural capturing ends, the radiation image capturing apparatus 1 is able to transmit the image data and other data by wireless communication to the console 20.

Figure 1B:
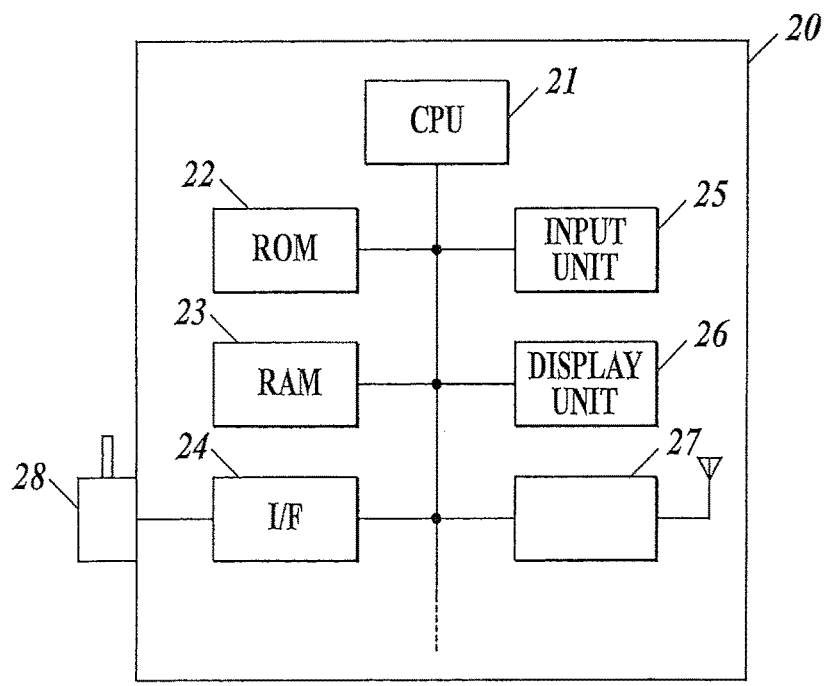
FIG. 1B is a block diagram showing a configuration of a console.

As shown in FIG. 1B, according to the present embodiment, the console 20 is configured as a computer including a CPU (Central Processing Unit) 21, a ROM (Read Only Memory) 22, a RAM (Random Access Memory) 23, an input/output interface 24, etc. and the like, and the above are connected to each other by a bus.

As shown in FIG. 1A and FIG. 1B, an input unit 25 such as a keyboard or a mouse and a display unit 26, including a CRT (Cathode Ray Tube), an LCD (Liquid Crystal Display), etc. are connected to the console 20. According to the present embodiment, the laptop type computer as the console 20 includes a wireless communication module inside such as an antenna on the rear side of the display unit 26 as the first wireless communication unit 27 which is able to receive image data transmitted from the radiation image capturing apparatus 1 as described above.

According to the present embodiment, the console 20 performs image processing on the image data transmitted from the radiation image capturing apparatus 1 and a radiation image, in other words, an image for diagnosis can be generated. Then, the console 20 transmits the information of the generated image for diagnosis to the above described host computer, or an external apparatus or system such as a QA station, PACS, etc. (hereinafter collectively referred to as external system So (see FIG. 1A)).

Therefore, according to the present embodiment, the console 20 includes, for example, a wireless module which can be attached and detached including a wireless antenna, etc. attached to the main body unit including the keyboard as the second wireless communication unit 28 which is connected to the external system So and which is able to perform wireless communication with an access point Apo of a network No such as an in-house network of a hospital.

Figures 2, 3:
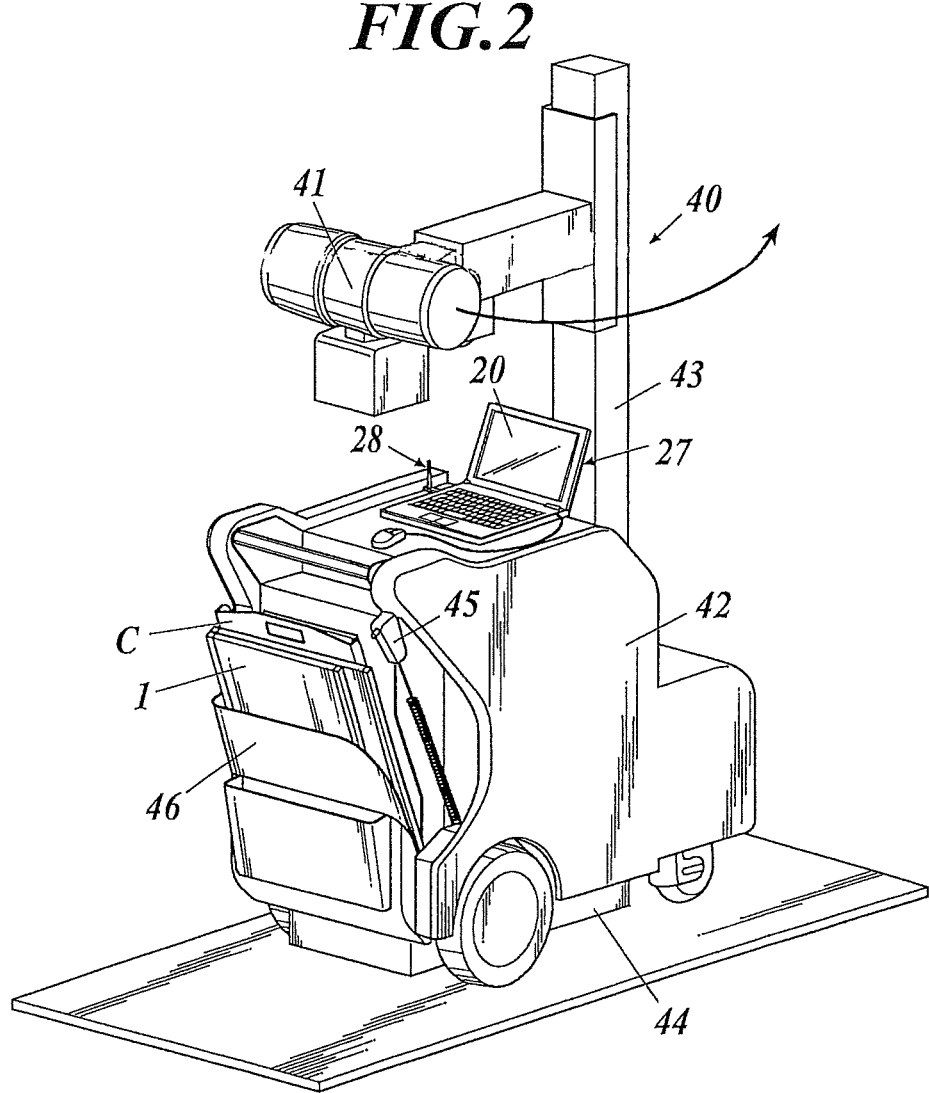
FIG. 2 is a diagram showing an example of a configuration of a radiation image capturing system structured on a diagnosis car.
FIG. 3 is a diagram showing an example of capturing order information.

As shown in FIG. 2, the console 20 of the present embodiment can be mounted on a diagnosis car 40. In this case, although illustration is omitted, the diagnosis car 40 can be moved to a hospital room, and the capturing can be performed in the hospital room, etc. Therefore, the diagnosis car 40 includes a portable radiation source 41. The radiation source 41 is provided above the main body unit 42 so as not to interfere with the movement of the diagnosis car 40. In capturing, for example, the radiation source 41 can be rotated around a support 43 as shown with an arrow in the figure.

A motor, etc. which is not shown to drive the radiation generating apparatus which irradiates radiation from the radiation source 41 or rotate wheels of the diagnosis car 40 is included in the main body unit 42 of the diagnosis car 40. An emitting switch 45 operated by the radiation technician to instruct irradiation of radiation to the radiation generating apparatus 44 is provided in a rear portion of the diagnosis car 40.

For example, the console 20, etc. which is a portable computer can be placed on the main body unit 42 of the diagnosis car 40. A cassette holder 46, etc. in which the radiation image capturing apparatus 1, the CR cassette C or the like can be stored is provided in the rear portion of the diagnosis car 40. The console 20 is placed on the main body unit 42, the radiation image capturing apparatus 1, etc. is stored in the cassette holder 46, and the console 20, the radiation image capturing apparatus 1, etc. can be conveyed together with the movement of the diagnosis car 40.

Although illustration is omitted, when the radiation image capturing apparatus 1 is conveyed to the hospital room, etc. as described above, the radiation image capturing apparatus 1 is used in capturing by inserting between the bed and the body of the patient or placing against the body of the patient. The console 20 is set in a position in each hospital room where the operator can easily operate the console 20 and the captured radiation image can be easily confirmed. As described above, each time the capturing ends or after a string of plural capturing ends, the image data and other data are transmitted from the radiation image capturing apparatus 1 to the console 20 by wireless communication.

[Configuration so that Wireless Communication does not Interfere]

Next, the configuration of the radiation image capturing system 100 of the present embodiment so that the wireless communication between the radiation image capturing apparatus 1 and the console 20 through the first wireless communication unit 27 does not interfere the wireless communication between the console 20 and the external system So through the second wireless communication unit 28 is described among several embodiments. The operation of the radiation image capturing system 100 according to each embodiment is also described.

[First Embodiment]

In order to prevent interference as described above, according to the first embodiment of the present invention, the console 20 gives priority to the wireless communication between the radiation image capturing apparatus 1 and the console 20 through the wireless communication unit 27 than the wireless communication between the console 20 and the external system So through the second wireless communication unit 28 so that both wireless communication are not performed at the same time. Examples of the configuration are provided below and described in detail.

[Configuration 1-1]

The radiation image capturing is largely divided into capturing in which the radiation image capturing apparatus 1 and the radiation generating apparatus 44 communicate with signals while synchronizing (hereinafter referred to as a linking method) or capturing in which there is no communication with signals between the radiation image capturing apparatus 1 and the radiation generating apparatus 44 (hereinafter referred to as non-linking method).

When capturing is performed by a non-linking method, usually, the radiation image capturing apparatus 1 itself detects the start of irradiation of radiation. Methods of the radiation image capturing apparatus 1 itself detecting start of irradiation of radiation are described in, for example, Japanese Patent Application Laid-Open Publication No. 2009-219538, WO 2011/135917, and WO 2011/152093.

Similar to when the radiation image capturing is performed with a non-linking method, when the radiation image capturing is performed with a linking method, the console 20 obtains the capturing order information as illustrated in FIG. 3 before capturing from the HIS or the RIS, which is one of the external systems So shown in FIG. 1A, through the above-described second wireless communication unit 28 (see FIG. 1A, FIG. 1B, and FIG. 2).

The capturing order information is information regarding the capturing and includes information regarding the patient who is the subject and information specifying the capturing conditions, etc. For example, as shown in FIG. 3, patient information such as "patient ID" P2, "patient name" P3, "sex" P4, "age" P5, "medical department" P6 and capturing conditions such as "capturing site" P7, "capturing direction" P8, and the like are set. Then, for example, "capturing order ID" P1 is assigned in the order that the capturing order is registered.

Then, when the radiation technician, etc. selects the capturing order information regarding the capturing to be performed from the capturing order information obtained by the console 20, the console 20 transmits all or a part of the selected capturing order information to the radiation image capturing apparatus 1 or the radiation generating apparatus 40 according to necessity. The console 20 starts control to start the radiation image capturing apparatus 1 to prepare for capturing.

Figure 4:
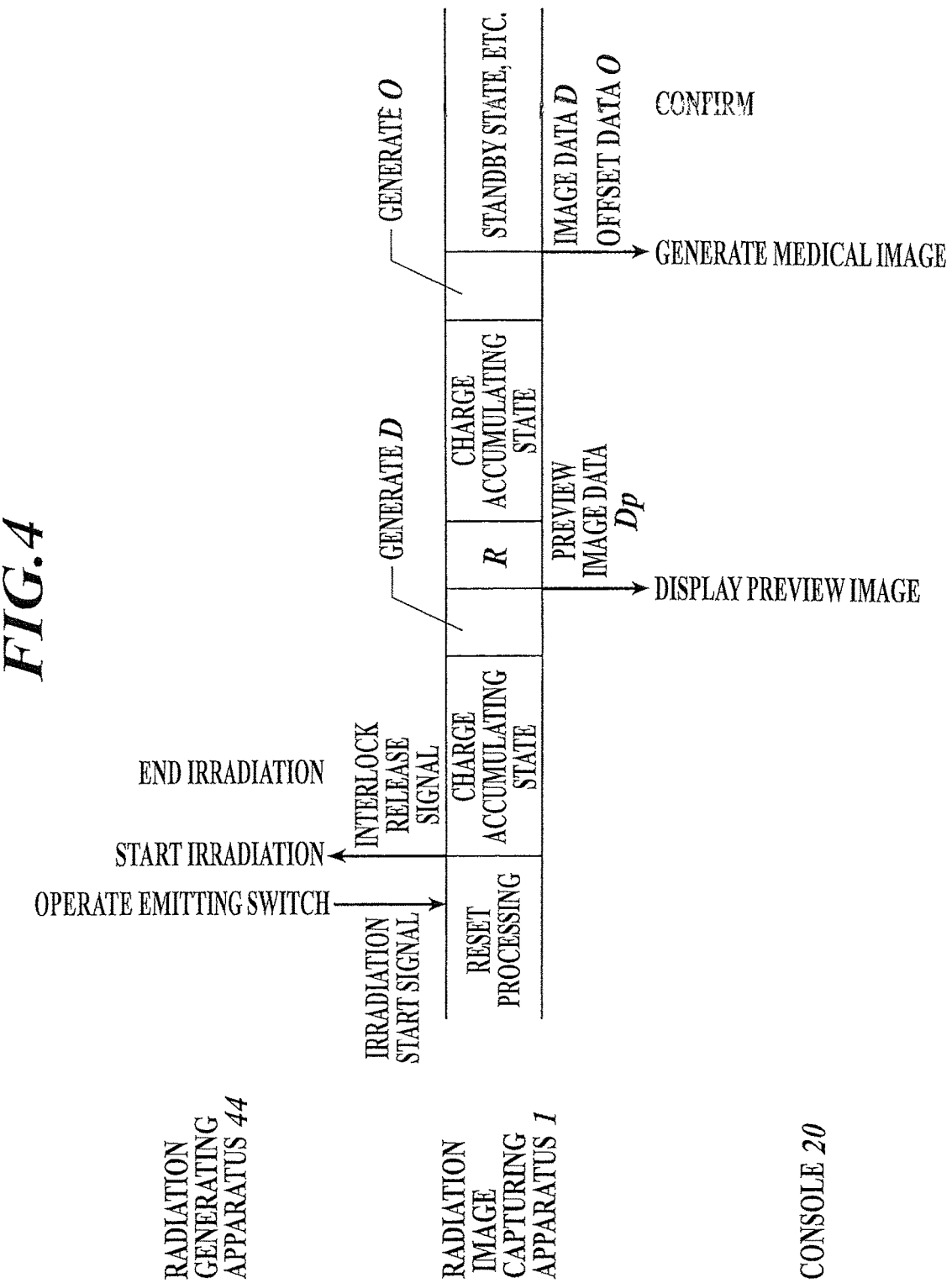
FIG. 4 is a diagram showing an example of a capturing sequence when capturing is performed in a linking format.

When capturing is performed in a linking method, the actual capturing is performed according to a capturing sequence such as that shown in FIG. 4. In other words, when the radiation technician operates the emitting switch 45 of the radiation generating apparatus 44 (see FIG. 2), the radiation generating apparatus 44 transmits an irradiation start signal through the console 20 to the radiation image capturing apparatus 1.

The radiation image capturing apparatus 1 performs reset processing in advance to remove charge remaining in the radiation detecting elements. When the irradiation start signal is transmitted from the radiation generating apparatus 44 as described above, the radiation image capturing apparatus 1 stops the reset processing of the radiation detecting element. Then, all of the switching elements of the radiation detecting elements are turned off. After advancing to the charge accumulated state in which the charge generated in each radiation detecting element according to the irradiated radiation is accumulated in each radiation detecting element, the radiation image capturing apparatus 1 transmits the interlock release signal through the console 20 to the radiation generating apparatus 44.

The irradiation of radiation from the radiation source 41 starts when the radiation generating apparatus 44 receives the interlock release signal from the radiation image capturing apparatus 1. Then, after radiation is irradiated for a set amount of irradiation time, the radiation generating apparatus 44 ends the irradiation of radiation.

When the irradiation of radiation ends, the radiation image capturing apparatus 1 reads the charge accumulated in the radiation detecting element with the read out circuit, generates the image data D for each radiation detecting element (see "generate D" in FIG. 4) and stores the generated image data D in the storage unit. Then, the radiation image capturing apparatus 1 extracts image data D at a certain percentage from the generated image data D and transmits by wireless communication the extracted image data D as the preview image data Dp to the console 20.

When the console 20 receives the preview image data Dp through the first wireless communication unit 27 (see FIG. 1A, FIG. 1B, FIG. 2), the console 20 generates the preview image p_pre based on the above data and displays the image on the display unit 26. The radiation technician views the displayed preview image p_pre and judges whether capturing needs to be performed again. When the radiation technician decides capturing does not need to be performed again, processing of generating the image for diagnosis performed by the radiation image capturing apparatus 1 and the console 20 (in other words, correction processing such as offset and gradation processing according to the site) is continued. When the radiation technician decides the capturing needs to be performed again, the processing performed by the radiation image capturing apparatus 1 and the console 20 is stopped and the capturing is performed again.

In a state before and after capturing in which the radiation is not irradiated, the radiation image capturing apparatus 1 repeats the sequence as described above, advancing from the reset processing of the radiation detecting element to the charge accumulated state and to the generating processing of the image data D. With this, the radiation image capturing apparatus 1 performs the generating processing of offset data O (see "generate O" in FIG. 4). "R" as shown in FIG. 4 shows the reset processing of the radiation detecting element when the generating processing of the offset data O is performed.

When the generating processing of the offset data O ends, the radiation image capturing apparatus 1 transmits the generated image data D, the image data D other than the preview image data Dp already transmitted or the generated offset data O to the console 20 by wireless communication.

When the console 20 receives the image data D or the offset data O through the first wireless communication unit 27, the console 20 generates the image p for diagnosis based on the above and displays the generated image p for diagnosis on the display unit 26. The radiation technician corrects the image p for diagnosis as necessary. Then, the radiation technician clicks the OK button icon displayed on the display unit 26.

Then, when the radiation technician approves the image p for diagnosis as described above, the console 20 associates the information of the image p for diagnosis with the capturing order information which the image p for diagnosis is based on and confirms the above. Then, the console 20 transmits the confirmed capturing order information, the information regarding the image p for diagnosis and the like to the host computer or the external system So (see FIG. 1A) such as the QA station, PACS, etc. through the second wireless communication unit 28.

The above is an example of the capturing sequence when the capturing is performed by a linking method. In such capturing sequence, for example, when the radiation image capturing apparatus 1 transmits the image data D generated by the radiation image capturing apparatus 1 in the next capturing to the console 20 while the confirmed image p for diagnosis and the capturing order information are transmitted from the console 20 to the external system So, the above-described interference may occur.

As described above, when the radiation technician operates the emitting switch 45 of the radiation generating apparatus 44, the radiation is irradiated for the radiation generating apparatus 44 and capturing is performed. The image data D is transmitted from the radiation image capturing apparatus 1 to the console 20. With this, according to the configuration 1-1, the operation of the emitting switch 45 by the radiation technician can function as a trigger, and when the emitting switch 45 is operated, the wireless communication between the console 20 and the external system So through the second wireless communication unit 28 can be prohibited.

According to the present embodiment, as described above, the radiation generating apparatus 44 communicates with the radiation image capturing apparatus 1 through the console 20. Alternatively, when the radiation technician operates the emitting switch 45, the radiation generating apparatus 44 can transmit the irradiation start signal to the radiation image capturing apparatus 1 in addition to the console 20. Alternatively, the radiation generating apparatus 44 can communicate directly with the radiation image capturing apparatus 1, and the radiation generating apparatus 44 can allow the radiation image capturing apparatus 1 which received the irradiation start signal to transmit the signal to the console 20. Alternatively, the interlock release signal transmitted from the radiation image capturing apparatus 1 to the radiation generating apparatus 44 can be transmitted to the console 20 also, and the console 20 can also acknowledge that the emitting switch 45 is operated.

According to the above configuration, by prohibiting wireless communication between the console 20 and the external system So through the second wireless communication unit 28 at least until the radiation image capturing apparatus 1 finishes transmitting the image data D and the offset data O, it is possible to reliably prevent interference between the wireless communication through the first wireless communication unit 27 (in other words, for example, transmitting the image data D, etc. from the radiation image capturing apparatus 1 to the console 20) and the wireless communication through the second wireless communication unit 28 (in other words, for example, transmitting the image p for diagnosis, capturing order information, etc. from the console 20 to the external system So).

When the wireless communication between the console 20 and the external system So through the second wireless communication unit 28 is prohibited while the image p for diagnosis, capturing order information, etc. are transmitted from the console 20 to the external system So through the second wireless communication unit 28, for example, when the wireless communication between the console 20 and the external system So through the second wireless communication 28 is allowed later, the console 20 resends the image p for diagnosis and capturing order information which was being transmitted or transmits the image p for diagnosis and capturing order information which was not yet transmitted.

When the radiation generating apparatus 44 communicates with the radiation image capturing apparatus 1 through the console 20, preferably, the interlock release signal is transmitted to the radiation generating apparatus 44 (emitting permit) at a timing when the wireless communication with the external system So is easily paused (for example, timing when transmission of one image p for diagnosis ends when a plurality of images p for diagnosis are transmitted).

[Configuration 1-2]

As shown in FIG. 4, there is time from when the radiation technician operates the emitting switch 45 of the radiation generating apparatus 44 until the image D, etc. is transmitted from the radiation image capturing apparatus 1 to the console 20. The time necessary for the generating processing of the offset data O to be completed from when the radiation image capturing apparatus 1 transmits the interlock release signal and the state is switched to the charge accumulating state is clear in advance.

Therefore, instead of prohibiting the wireless communication between the console 20 and the external system So through the second wireless communication unit 28 immediately when the emitting switch 45 of the radiation generating apparatus 44 is operated as described in configuration 1-1, it is possible to prohibit wireless communication through the second wireless communication unit 28 at the point when a predetermined amount of time passes after the emitting switch 45 is operated.

According to the configuration as described above, similar to the configuration 1-1, the interference between the wireless communication through the first wireless communication unit 27 and the wireless communication through the second wireless communication unit 28 can be reliably prevented.

Moreover, for example, when the emitting switch 45 of the radiation generating apparatus 44 is operated, the console 20 may be able to calculate the data amount that can be transmitted to the external system So within the above predetermined amount of time, and transmit data (for example, information of the image p for diagnosis and the capturing order information) no more than the above amount of data within the above predetermined amount of time. According to the above configuration, it is possible to prevent the transmission of data being cut while the data is transmitted through the second wireless communication unit, and it is possible to reliably prevent data from being damaged.

[Configuration 2-1]

Turning to the non-linking method, the actual capturing is performed by the capturing sequence such as that shown in FIG. 5. In other words, unlike the linking method shown in FIG. 4, detecting processing of the start of irradiation of radiation is performed in the radiation image capturing apparatus 1 instead of or parallel with the reset processing of the radiation detecting element.

Even if the radiation technician operates the emitting switch 45 of the radiation generating apparatus 44, unlike the linking method, the irradiation start signal is not transmitted from the radiation generating apparatus 44 to the radiation image capturing apparatus 1 (therefore, the interlock release signal is not transmitted from the radiation image capturing apparatus 1 to the radiation generating apparatus 44) and the radiation is irradiated from the radiation generating apparatus 44.

When the start of irradiation of radiation is detected, the radiation image capturing apparatus 1 immediately turns off all of the switch elements of the radiation detecting elements and advances to the charge accumulating state. Then, the processing after the generating processing of the image data D (see "generate D" in FIG. 5) is basically the same as the linking method.

As described above, when the capturing is performed by the non-linking method, the console 20 is not able to acknowledge that the emitting switch 45 is operated by the configuration as described in the linking method such as transmitting the irradiation start signal transmitted from the radiation generating apparatus 44 to the radiation image capturing apparatus 1 when the radiation technician operates the emitting switch 45 to the console 20 or transmitting the interlock release signal transmitted from the radiation image capturing apparatus 1 to the radiation generating apparatus 44 to the console 20.

Therefore, a unit to detect that the radiation technician operated the emitting switch 45 of the radiation generating apparatus 44 or a unit to detect that the emitting switch 45 is in an operable state is provided so that when the above unit detects that the emitting switch 45 is operated or operable, the console 20 can prohibit wireless communication through the second wireless communication unit 28.

Figure 6A:
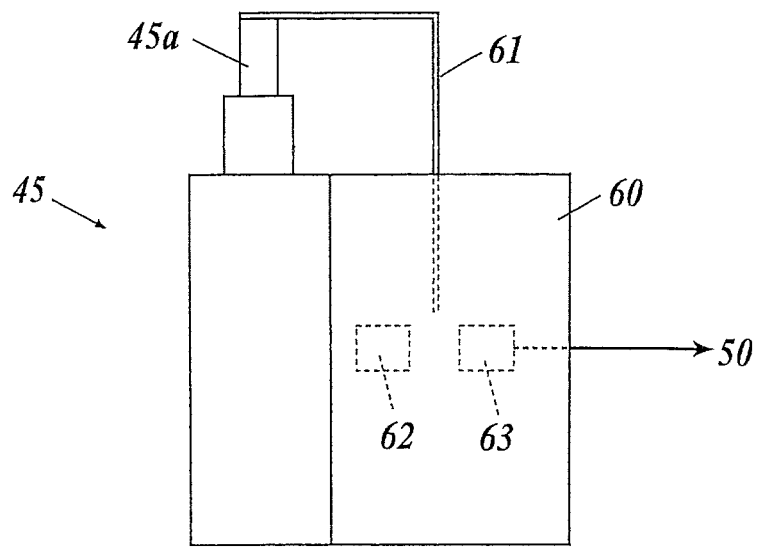
FIG. 6A is a diagram showing a detecting unit as an example of a unit to detect whether an emitting switch of the radiation generating apparatus is operated.
Figure 6B:
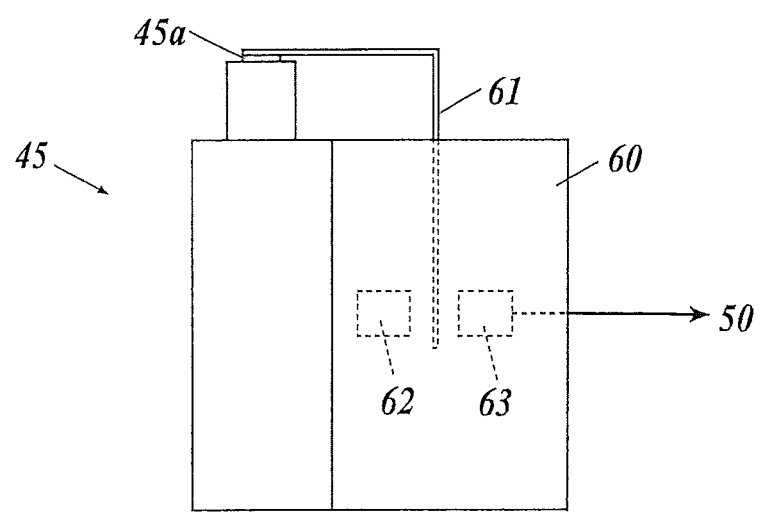
FIG. 6B is a diagram showing a detecting unit as an example of a unit to detect whether an emitting switch of the radiation generating apparatus is operated.

It is possible to attach a detecting unit 60 as shown in FIG. 6 to the emitting switch 45 as a unit to detect that the radiation technician operated the emitting switch 45 of the radiation generating apparatus 44. An example of the detecting unit 60 is configured as follows. For example, one end of a movable piece 61 in a substantial L shape is attached to a tip of a button 45a of the emitting switch 45. When the button 45a of the emitting switch 45 is pressed and the movable piece 61 moves, the other edge of the movable piece 61 blocks the light emitted from a light emitting element 62 to a light receiving element 63. With this, it is possible to detect the radiation technician operated the emitting switch 45.

Figure 7:
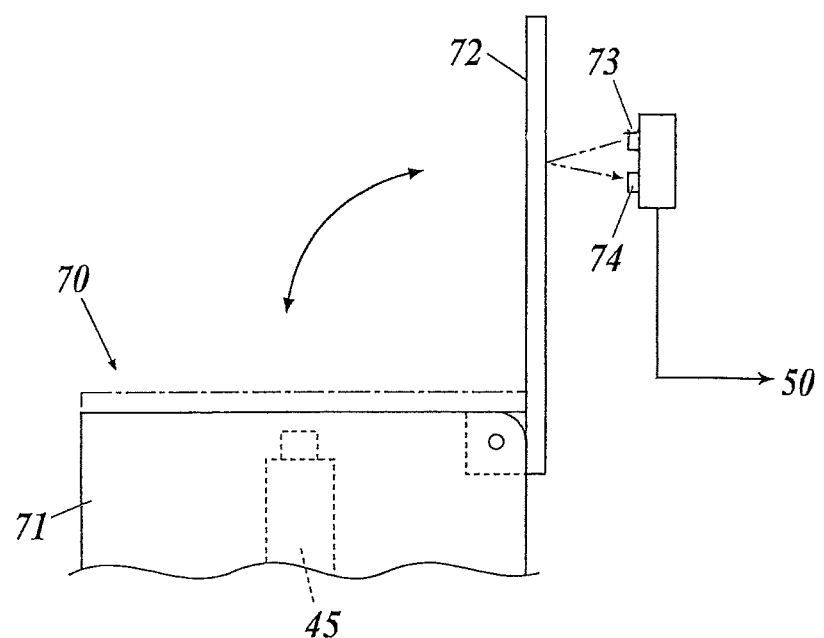
FIG. 7 is a diagram showing a cover apparatus as an example of a unit to detect whether an emitting switch of the radiation generating apparatus is in an operable state.

For example, a cover device 70 as shown in FIG. 7 can be provided as a unit to detect that the emitting switch 45 of the radiation generating apparatus 44 is in an operable state. The emitting switch 45 is stored in a main body unit 71 of the cover device 70. The radiation technician cannot operate the emitting switch 45 without opening a lid 72 of the cover device 70.

The cover device 70 is configured so that a light emitting element 73 and a light receiving element 74 are provided in a position where light emitted from the light emitting element 73 is reflected on the lid 72 and received by the light receiving element 74 when the lid 72 is opened. With this, it is possible to detect that the emitting switch 45 is in an operable state (here, the lid 72 is open).

[Configuration 2-2]

Similar to the configuration 1-2, instead of the console 20 immediately prohibiting the wireless communication between the console 20 and the external system So through the second wireless communication unit 28 when the detecting signal is transmitted from the detecting unit 60 or the cover device 70 as in the configuration 2-1, the wireless communication through the second wireless communication unit 28 can be prohibited after a predetermined amount of time passes from when the detecting signal is transmitted. According to the above configuration, advantageous effects similar to the configuration 1-2 can be obtained.

According to the above description, the configuration 2-1 and the configuration 2-2 are described as being applied in a radiation image capturing system 100 which performs capturing with a non-linking method. Alternatively, the configuration 2-1 and the configuration 2-2 can be applied to the radiation image capturing system 100 which performs capturing with a linking method.

[Configuration 3]

According to the configuration 1-1 to configuration 2-2, the radiation technician operating the emitting switch 45 of the radiation generating apparatus 44 functions as a trigger, and from then on, the wireless communication between the console 20 and the external system So through the second wireless communication unit 28 is prohibited. With this, the wireless communication between the radiation image capturing apparatus 1 and the console 20 through the first wireless communication unit 27 is put ahead of the wireless communication between the console 20 and the external system So through the second wireless communication unit 28.

However, items other than operating the emitting switch 45 can be applied as the trigger to prohibit wireless communication between the console 20 and the external system So through the second wireless communication unit 28.

For example, when capturing is performed by either the linking method or the non-linking method, as described above, before capturing, the radiation technician selects the capturing order information regarding the capturing to be performed from the capturing order information obtained by the console 20. In other words, the capturing starts when the radiation technician selects the capturing order information.

Therefore, in the configuration 3, for example, the radiation technician selecting the capturing order information regarding the capturing to be performed functions as the trigger, and the console 20 prohibits wireless communication through the second wireless communication unit 28 when the capturing order information regarding the capturing to be performed is selected from the obtained capturing order information.

According to the above configuration, while the capturing order information is selected and the capturing is performed, in other words, while the image data D and the offset data O are transmitted from the radiation image capturing apparatus 1, the wireless communication through the second wireless communication unit 28 is prohibited. Therefore, similar to the above configuration, it is possible to reliably prevent interference between the wireless communication through the first wireless communication unit 27 and the wireless communication through the second wireless communication unit 28.

According to the configuration 3, similar to the above-described configuration 1-2 and configuration 2-2, instead of immediately prohibiting the wireless communication between the console 20 and the external system So through the second wireless communication 28 when the capturing order information is selected, the wireless communication through the second wireless communication unit 28 can be prohibited when a predetermined amount of time passes from when the capturing order information is selected. According to the above configuration, the advantageous effects as described in the configuration 1-2 and the configuration 2-2 can be achieved.

[Configuration 4]

Regardless of whether the capturing is performed by the linking method or the non-linking method, when the irradiation of radiation on the radiation image capturing apparatus 1 ends and the generating processing of the image data D is performed, the preview image Dp is transmitted from the radiation image capturing apparatus 1 to the console 20. Depending on the configuration of the radiation image capturing system 100, instead of the preview image data Dp extracted from the image data D, the image data D itself (raw data) may be transmitted when the generating processing of the image data D ends in the radiation image capturing apparatus 1.

Therefore, in configuration 4, for example, the preview image data Dp or the image data D being transmitted from the radiation image capturing apparatus 1 to the console 20 may function as the trigger, and the console 20 prohibits wireless communication through the second wireless communication unit 28 when the preview image data Dp or the image data D is transmitted. In this case, the wireless communication through the second wireless communication unit 28 is immediately cut when the preview image data Dp or the image data D is transmitted.

According to the above configuration, if wireless communication between the console 20 and the external system So through the second wireless communication unit 28 is performed when the preview image data Dp or the image data D is transmitted from the radiation image capturing apparatus 1 to the console 20, interference may occur at this moment. However, since the wireless communication through the second wireless communication unit 28 is immediately cut, at least interference from then on does not occur.

Therefore, from then on, since the wireless communication through the second wireless communication unit 28 is prohibited until the necessary data such as the offset data O is transmitted from the radiation image capturing apparatus 1 and the capturing ends, similar to the above configuration, it is possible to reliably prevent the interference between the wireless communication through the first wireless communication unit 27 and the wireless communication through the second wireless communication unit 28. Moreover, since time-out error in the communication is suppressed, it is possible to overcome the risk of losing the image due to error in operation of processing of recovering from the time-out error.

[Configuration 5]

Regardless of whether the capturing is performed by the linking method or the non-linking method, when the radiation is irradiated once from the radiation generating apparatus 44 for each patient (subject), and capturing is performed once for each person, each time the capturing for one patient ends, the radiation technician brings the radiation image capturing apparatus 1 to the next patient or requests the present patient to change with the next patient and places the radiation image capturing apparatus 1 against the next patient to position the radiation image capturing apparatus 1. With this, the next capturing is performed. Therefore, when the capturing is performed once for each patient, a relatively large amount of time is consumed from when the capturing ends until the next capturing is performed.

Therefore, in such case, usually, while the radiation technician performs positioning of the radiation image capturing apparatus 1 after the present capturing ends, the console 20 finishes the generating processing of the image p for diagnosis based on the image data D, the offset data O, etc. transmitted from the radiation image capturing apparatus 1 according to the finished capturing, and the processing of associating and confirming the image with the capturing order information (see FIG. 4 and FIG. 5). With this, it is possible to finish transmitting the associated image for diagnosis and capturing order information to the external system So.

As described in the above configurations, the wireless communication through the second wireless communication unit 28 may be prohibited before the console 2 finishes transmitting the associated image for diagnosis and the capturing order information to the external system So.

For example, when the capturing is performed a plurality of times for one patient (one subject), each time capturing ends, the positioning of the radiation image capturing apparatus 1 is changed for the same patient or the posture of the patient with respect to the radiation image capturing apparatus 1 is changed. Therefore, only a relatively short amount of time is necessary to finish the positioning and then the next capturing is performed. Consequently, the time necessary for each capturing becomes short.

Therefore, in such situation, if the image p for diagnosis is generated in the console 20 based on the transmitted image D, etc. transmitted from the radiation image capturing apparatus 1 and the image p for diagnosis, etc. is transmitted to the external system So for each capturing, the image data D obtained in the next capturing may be transmitted from the radiation image capturing apparatus 1 to the console 20 while the image p for diagnosis, etc. is transmitted from the console 20 to the external system So.

Therefore, when capturing is performed a plurality of times on one patient (one subject), and the image for diagnosis is transmitted from the console 20 to the external system So for each capturing, there is a high possibility that the wireless communication through the first wireless communication unit 27 interferes with the wireless communication through the second wireless communication unit 28.

However, when a string of a plurality of capturing ends for one patient and the capturing advances to the next patient, as described above, the patient needs to be changed or the radiation image capturing apparatus 1 needs to be moved and positioned. Therefore, the interval until the next capturing becomes long.

As described above, for example, when the capturing order information is selected, and a plurality of pieces of capturing order information is selected for the same person so that the capturing is performed a plurality of times for the same patient (same subject), the wireless communication through the second wireless communication unit can be prohibited until the series of plurality of capturing of the patient ends. When the series of plurality of capturing of the patient ends, the image p for diagnosis and the capturing order information for the plurality of capturing can be collectively transmitted to the external system So through the second wireless communication unit 28.

In the actual radiation image capturing system 100, other than performing capturing a plurality of times for one patient, a plurality of groups of the image p for diagnosis and the capturing order information may be transmitted collectively in groups from the console 20 to the external system So. However, the time consumed for wireless communication from the console 20 to the external system So through the second wireless communication unit 28 becomes relatively long, and the possibility that such wireless communication interferes with the wireless communication through the first wireless communication unit 27 becomes high.

Therefore, when the image p for diagnosis is transmitted from the console 20 to the external system So, preferably, the image p for diagnosis is transmitted one image at a time, in other words, the group including the image p for diagnosis and the capturing order information is transmitted one group at a time to the external system So through the second wireless communication unit 28. Here, preferably, the image p for diagnosis is transmitted one image at a time with the amount of time necessary to perform one capturing provided as an interval.

According to the above configuration, the time consumed for wireless communication from the console 20 to the external system So through the second wireless communication unit becomes short, and the possibility that the wireless communication interferes with the wireless communication through the first wireless communication unit 27 becomes lower. Even if interference occurs, it is possible to prevent the wireless communication through the second wireless communication unit 28 becoming long and time-out occurring. At least, it is possible to prevent the image data D and the information of the image p for diagnosis from being lost.

[Configuration 6]

As a variation of putting priority on the wireless communication through the first wireless communication unit 27 as described in the first embodiment, the following configuration is possible. For example, when the radiation image capturing apparatus 1 is able to perform capturing, the console 20 prohibits wireless communication through the second wireless communication unit 28, and only when the radiation image capturing apparatus 1 cannot be used for capturing, the wireless communication through the second wireless communication unit 28 is allowed.

In this case, examples in which the radiation image capturing apparatus 1 cannot be used for capturing include, when the power of the radiation image capturing apparatus 1 is off, or when the radiation image capturing apparatus 1 is in a sleep state (also called power saving mode). Alternatively, for example, an acceleration sensor can be attached to the radiation image capturing apparatus 1 or a handle can be provided on the radiation image capturing apparatus 1 and a unit for detecting when the radiation technician holds the handle can be provided. With this, it is possible to detect that the radiation image capturing apparatus 1 is being moved, and thus cannot be used for capturing.

According to the above configuration, the wireless communication between the console 20 and the external system So through the second wireless communication unit 28 is performed only when it is certain that the image data D, etc. is not transmitted from the radiation image capturing apparatus 1. Therefore, it is possible to reliably prevent interference between the wireless communication through the first wireless communication unit 27 and the wireless communication through the second wireless communication unit 28.

[Second Embodiment]

According to the first embodiment, in order to prevent interference between the wireless communication through the first wireless communication unit 27 and the wireless communication through the second wireless communication unit 28, the console 20 gives priority to the wireless communication between the radiation image capturing apparatus 1 and the console 20 through the first wireless communication unit 27.

According to the second embodiment of the present invention described next, in order to prevent interference between the wireless communication through the first wireless communication unit 27 and the wireless communication through the second wireless communication unit 28, the console 20 gives priority to the wireless communication between the console 20 and the external system So through the second wireless communication unit 28.

[Configuration 7]

In this case, for example, the capturing may not be performed while the console performs wireless communication through the second wireless communication unit 28. In other words, when the console 20 is performing wireless communication through the second wireless communication unit 28, the irradiation of radiation from the radiation generating apparatus 44 can be prohibited until the wireless communication through the second wireless communication unit 28 ends.

According to the above configuration, while the console 20 is performing the wireless communication through the second wireless communication unit 28, the image data D, etc. is not transmitted from the radiation image capturing apparatus 1 through the first wireless communication unit 27. Therefore, interference does not occur between the wireless communication through the first wireless communication unit 27 and the wireless communication through the second wireless communication unit 28.

As a method to realize the above, the following configuration is possible. For example, in capturing performed by the above-described linking method, when the radiation technician operates the emitting switch 45 of the radiation generating apparatus 44 and the irradiation start signal is transmitted from the radiation generating apparatus 44 to the radiation image capturing apparatus 1, the radiation image capturing apparatus 1 transmits a signal inquiring to the console 20 whether the interlock release signal can be transmitted to the radiation generating apparatus 44 and when an allowance signal is transmitted from the console 20, the radiation image capturing apparatus 1 transmits the interlock release signal to the radiation generating apparatus 44.

According to the above configuration, if the console 20 does not transmit the allowance signal to the radiation image capturing apparatus 1 until the wireless communication through the second wireless communication unit 28 ends, a configuration is possible in which the radiation is not irradiated from the radiation generating apparatus 44 (in other words, the irradiation of radiation is prohibited) until the console 20 ends the wireless communication through the second wireless communication unit 28.

Regardless of whether the capturing is performed by the linking method or the non-linking method, it is possible to provide a warning unit which warns the radiation technician not to irradiate radiation by notifying through display or sound that the console 20 is performing wireless communication through the second wireless communication unit 28. In this case, for example, the console 20 is able to function as the warning unit by displaying a warning on the display unit 26 or making a sound. Moreover, a warning unit can be provided on the diagnosis car 40 (see FIG. 2).

For example, the detecting unit 60 as shown in FIG. 6 or the cover device 70 shown in FIG. 7 can be used and when the signal transmitted from the console 20 when the console 20 performs the wireless communication through the second wireless communication unit 28 is received, the movable piece 61 of the detecting unit 60 can be made so as not to move or the lid 72 of the cover device 70 can be made so as not to open so that the radiation technician cannot operate the emitting switch 45.

[Configuration 8]

Similar in both the linking method and the non-linking method, it is preferable that when an emergency patient is captured in the radiation image capturing system 100, the image data D, etc. is transmitted from the radiation image capturing apparatus 1 to the console 20 immediately after capturing the patient, the image p for diagnosis is generated in the console 20 and transmitted to the external reading terminal, etc., and the image p for diagnosis is displayed on the reading terminal so that the physician can promptly see the image and make a diagnosis.

Therefore, in such case also, preferably, the console 20 gives priority to the wireless communication with the external system So (for example, the reading terminal) through the second wireless communication unit 28 than the wireless communication with the radiation image capturing apparatus 1 through the first wireless communication unit 27. However, at the same time, when the patient is an emergency patient, it is desired that the sites of the body of the patient that need to be captured are captured continuously. Therefore, if the irradiation of radiation from the radiation generating apparatus 44 is prohibited as in configuration 7, in order to give priority to the wireless communication through the second wireless communication unit 28, capturing cannot be performed.

Therefore, in the configuration 8, the console 20 prohibits wireless communication through the first wireless communication unit 27 while the wireless communication through the second wireless communication unit 28 is performed, and only when the wireless communication through the second wireless communication unit 28 is not performed, the wireless communication through the first wireless communication unit 27 is allowed.

In this case, even when the console 20 is performing wireless communication through the second wireless communication unit 28 and the wireless communication through the first wireless communication unit 27 cannot be performed, the radiation technician is able to irradiate radiation from the radiation generating apparatus 44 to the radiation image capturing apparatus 1 and the capturing can be performed.

For example, the radiation image capturing apparatus 1 transmits a request for transmission of the image data D, etc. to the console 20, and the console 20 returns a signal which prohibits transmission to the radiation image capturing apparatus 1 while the wireless communication through the second wireless communication unit 28 is performed. A signal to allow transmission can be returned to the image capturing apparatus 1 when the wireless communication through the second wireless communication unit 28 is not performed.

According to the above configuration, the console 20 is able to give priority to the wireless communication with the external system So through the second wireless communication unit 28 while the wireless communication through the second wireless communication unit 28 is performed, and the radiation image capturing apparatus 1 is able to continue capturing during the above. The image data D, etc. stored in the storage unit can be transmitted after the console 20 ends the wireless communication through the second wireless communication unit 28.

Therefore, for example, the console 20 is able to transmit with priority information of the image p for diagnosis capturing the emergency patient to the external reading terminal and capturing of the emergency patient using the radiation image capturing apparatus 1 can be performed continuously. With this, the physician is able to perform diagnosis of the emergency patient reliably and promptly.

[Third Embodiment]

According to the first embodiment and the second embodiment, whether the console 20 gives priority to the wireless communication through the first wireless communication unit 27 or the wireless communication through the second wireless communication unit 28 is set in advance. However, it is possible to configure the present invention so that the console 20 is able to switch the preferential wireless communication between the wireless communication through the first wireless communication unit 27 and the wireless communication through the second wireless communication unit 28 depending on the situation.

[Configuration 9]

For example, when the radiation image capturing apparatus 1 is portable as described in the present invention, one radiation image capturing apparatus 1 can be used in a plurality of diagnosis cars 40. Since there is a difference in the performance of the radiation source 41, the irradiation characteristics of the radiation, and the like according to each radiation generating apparatus 44 loaded on the diagnosis car 40, for example, the amount of time that the charge accumulating state is continued as shown in FIG. 4 and FIG. 5 may need to be set to a longer time.

When the time that the charge accumulating state continues becomes long, the time that the charge accumulating state continues before the generating processing of the offset data 0 (see "generate O" in figure) performed later on as shown in FIG. 4 and FIG. 5 becomes longer. Therefore, for example, the time from when the radiation technician operates the emitting switch 45 of the radiation generating apparatus 44 and irradiates the radiation to when the image data D and the offset data O is transmitted from the radiation image capturing apparatus 1 to the console 20 becomes longer than when the time that the charge accumulating state continues is set to a short time.

When the console 20 gives priority to the wireless communication through the first wireless communication unit 27 than the wireless communication through the second wireless communication unit 28 even when the time that the charge accumulating state continues is set to a long time, the information of the image p for diagnosis associated with the capturing order information cannot be transmitted from the console 20 to the external system So through the second wireless communication unit 28 for a long period of time until the image data D and the offset data O are transmitted.

However, the efficiency of the capturing including the process up to transmitting the image p for diagnosis to the external system So drastically reduces. Rather, in the above case, the efficiency of capturing is enhanced when the wireless communication through the second wireless communication unit 28 is given priority over the wireless communication through the first wireless communication unit 27.

On the other hand, if the console 20 always gives priority to the wireless communication through the second wireless communication unit 28 than the wireless communication through the first wireless communication unit 27, for example, when the console 20 transmits a large amount of information of the image p for diagnosis to the external system So through the second wireless communication unit 28, the image data D, etc. cannot be transmitted from the radiation image capturing apparatus 1 to the console 20 through the first wireless communication unit 27.

When the state that the image data D, etc. cannot be transmitted from the radiation image capturing apparatus 1 to the console 20 continues, and the capturing using the radiation image capturing apparatus 1 is performed continuously, the amount of the image data D, etc. stored in the storage unit of the radiation image capturing apparatus 1 exceeds the capacity of the storage unit, and the capturing using the radiation image capturing apparatus 1 cannot be performed.

For example, when only one radiation image capturing apparatus 1 is loaded on the diagnosis car 40 shown in FIG. 2, there is no substitute radiation image capturing apparatus 1 and the next capturing cannot be performed until the image data D, etc. stored in the storage unit of the radiation image capturing apparatus 1 is transmitted to the console 20. Alternatively, the radiation technician needs to bring another radiation image capturing apparatus 1 from a storage site, and this may be troublesome to the radiation technician.

For example, the length of time that the charge accumulating state continues is set in the radiation image capturing apparatus 1 in capturing, and depending on the set length of time, the console 20 is able to switch the preferential wireless communication between the wireless communication through the first wireless communication unit 27 and wireless communication through the second wireless communication unit 28.

For example, in the above case, when the length of time that the charge accumulating state continues set in the radiation image capturing apparatus 1 in capturing is equal to or less than a set threshold, the console 20 switches so that the wireless communication through the first wireless communication unit 27 is given priority, and when the set length of time that the charge accumulating state continues is longer than the set threshold, the console 20 switches so that the wireless communication through the second wireless communication unit 28 is given priority.

According to the above configuration, it is possible to reliably prevent the above problems and to reliably enhance the efficiency of capturing. Moreover, it is not troublesome for the radiation technician, and it is possible to provide a radiation image capturing system 100 which is easy to use for the radiation technician.

In this case, information regarding the set length of time that the charge accumulating state continues can be transmitted from the radiation image capturing apparatus 1 to the console 20. Alternatively, for example, the radiation technician may input to the console 20 the identification information of the diagnosis car 40 or the radiation source 41 to be used in capturing. A table associating the identification information and the time that the charge accumulating state continues can be stored in advance in the console 20. The table can be referred to obtain the length of time that the charge accumulating state continues set in the radiation image capturing apparatus 1 in capturing.

Alternatively, the console 20 may be provided in advance with a table associating the identification information of the diagnosis car 40 and the radiation source 41 with the first wireless communication unit 27 or the second wireless communication unit 28. When the identification information of the diagnosis car 40 or the radiation source 41 is input, based on the above table, the console 20 may be able to directly determine the wireless communication to be given priority between the wireless communication through the first wireless communication unit 27 and the wireless communication through the second wireless communication unit 28.

[Configuration 10]

According to the configuration 9, the console 20 automatically switches the preferential wireless communication between the wireless communication through the first wireless communication unit 27 and wireless communication through the second wireless communication unit 28 based on the length of time that the charge accumulating state continues set in the radiation image capturing apparatus 1.

However, for example, the radiation technician can instruct the console 20 to switch the preferential wireless communication between the wireless communication through the first wireless communication unit 27 and wireless communication through the second wireless communication unit 28 according to necessity.

In other words, for example, when capturing is performed a plurality of times for one patient, the image data D, the offset data O, etc. are transmitted from the radiation image capturing apparatus 1 each time the capturing ends. Therefore, the console 20 switches so that the wireless communication through the first wireless communication unit 27 is given priority. When the capturing is performed once for each patient, since changing the patient consumes much time, the interval that the image data D is transmitted from the radiation image capturing apparatus 1 becomes long. Therefore, in such case, the console 20 switches so that the wireless communication through the second wireless communication unit 28 is given priority.

For example, when the capturing is performed a plurality of times on an elderly patient, a patient with a serious condition, or a patient who must have rest, the posture of the patient may be changed for each capturing, and with this, the interval between capturing may become long. Therefore, for example, in such case, even if capturing is performed a plurality of times on one patient, the console 20 can switch to give priority to the wireless communication with the external system So through the second wireless communication unit 28.

As described above, depending on the age and the medical condition of the patient, the console 20 may switch the preferential wireless communication between the wireless communication through the first wireless communication unit 27 and the wireless communication through the second wireless communication unit 28.

Further, the radiation technician may set the console 20 to switch the preferential wireless communication between the wireless communication through the first wireless communication unit 27 and the wireless communication through the second wireless communication unit 28 depending on whether a normal patient is captured or an emergency patient is captured.

In other words, in this case, when a normal patient is captured, the preferential wireless communication is switched to the wireless communication through the first wireless communication unit 27 to transmit the image data D, etc. from the radiation image capturing apparatus 1 to the console 20. When an emergency patient is captured, the transmission of the image p for diagnosis, etc. from the console 20 to the external system So such as the reading terminal, etc. is given priority. Therefore, the preferential wireless communication is switched and the wireless communication through the second wireless communication unit 28 is given priority.

As described above, according to the situation, the radiation technician can determine the preferential wireless communication that the console 20 switches to between the wireless communication through the first wireless communication unit 27 and the wireless communication through the second wireless communication unit 28. With this, the capturing can be suitably performed and the efficiency of capturing can be enhanced.

[Fourth Embodiment]

[Configuration 11]

The following configuration is possible in order to simply solve the problem to be solved by the present invention which is to not cause interference between the transmission of the image data D from the radiation image capturing apparatus 1 to the console 20 by wireless communication (in other words, wireless communication through the first wireless communication unit 27) and the wireless communication between the console 20 and the external system So (in other words, the wireless communication through the second wireless communication unit 28).

In other words, when the wireless communication through the first wireless communication unit 27 and the wireless communication through the second wireless communication unit 28 both use the same channel as the wireless communication channel used in the facility such as the hospital in which the radiation image capturing system 100 is applied, for example, the arbitration function of the wireless LAN is able to arbitrate the wireless communication among the wireless communication through the first wireless communication unit 27, the wireless communication through the second wireless communication unit 28, and the wireless communication with other devices in the facility. Therefore, at least the interference between the wireless communication through the first wireless communication unit 27 and the wireless communication through the second wireless communication unit 28 can be reliably prevented.

As described above, for example, the information of the channel used in the facility can be input in the console 20 in advance or when the console 20 is moved to the hospital room (capturing site), the area can be surveyed with the console 20, etc. to obtain information of the channel used in the facility, and in the capturing site, the console 20 may use the channel the same as the channel of the wireless communication used in the facility for both the wireless communication through the first wireless communication unit 27 and the wireless communication through the second wireless communication unit 28.

Therefore, for example, it is possible to reliably prevent the interference between the transmission of the image data D, etc. from the radiation image capturing apparatus 1 to the console 20 and the transmission of information of the image p for diagnosis from the console 20 to the external system So. Moreover, it is possible to reliably prevent error of the wireless communication between the radiation image capturing apparatus 1 and the console 20 or the wireless communication between the console 20 and the external system So due to timeout, and to prevent the image data D and the information of the image p for diagnosis from being lost when recovering from the error.

[Configuration 12]

It is well known that when the channel (in other words, frequency band) used in two wireless communication systems are apart 2 channels or more, interference does not occur between the two wireless communication systems. Therefore, the console 20 may set the channel used in the wireless communication through the first wireless communication unit 27 and the channel used in the wireless communication through the second wireless communication unit 28 in a channel at least 2 channels apart in each capturing site. Then, the wireless communication through the first wireless communication unit 27 and the wireless communication through the second wireless communication unit 28 are performed in each channel.

In this case, the wireless network already provided in the facility such as the hospital is mostly used for the wireless communication between the console 20 and the host computer or an external system So such as the QA station, PACS, HIS, RIS, etc. Therefore, for example, the console 20 sets the channel used for the wireless communication through the first wireless communication unit 27 at least 2 channels apart from the channel used for the wireless communication through the second wireless communication unit 28 and the wireless communication through the first wireless communication unit 27 is performed using such channel.

[Effect]

As described above, according to the radiation image capturing system 100 of the above-described embodiments, it is possible to reliably prevent interference between the transmission of the image data D by wireless communication from the radiation image capturing apparatus 1 to the console 20 through the first wireless communication unit 27 and the wireless communication between the console 20 and the external system So through the second wireless communication unit 28.

Consequently, it is possible to reliably prevent timeout occurring in the transmission of the image data D, etc. from the radiation image capturing apparatus 1 to the console 20 and the transmission of the information of the image p for diagnosis from the console 20 to the external system So due to interference, and error occurring in communication. With this, it is possible to reliably prevent image data D and information of image p for diagnosis from being lost.

As shown in FIG. 1A, FIG. 1B, and FIG. 2, instead of directly connecting the wireless antenna, etc. as the second wireless communication unit 28 to the main body unit of the console 20, although illustration is omitted, in order to prevent interference, for example, the cable from the main body unit of the console 20 can be made longer and the wireless antenna, etc. can be attached to the tip so that the first wireless communication unit 27 (as described above, the antenna is usually provided on the rear side of the display unit in commercially available computers) and the second wireless communication unit 28 are made as far apart as possible.

[Problem of Switching Access Point]

For example, as described above, usually the wireless network already provided in the facility such as the hospital is used for the wireless communication between the console 20 loaded on the diagnosis car 40 (the same when the console 20, etc. is moved by the radiation technician) and the host computer or the external system So such as the QA station.

In this case, usually, the access point AP (for example, see Apo in FIG. 1A) of the wireless network is provided in a plurality of places in the facility, and when the console 20 is moved within the facility loaded on the diagnosis car 40 or carried by the radiation technician, the access point AP performing wireless communication with the console 20 is sequentially switched, and the wireless communication between the console 20 and the external system So is maintained through any access point AP of the wireless network.

However, as a result of research by the present inventors, the access points AP did not properly switch when the console 20 was moved. Therefore, the following problems may occur, for example, the time necessary to transmit the information of the image p for diagnosis from the console 20 to the external system So becomes unusually long, or in the worst case, the wireless communication between the console 20 and the wireless network is cut and the wireless communication between the console 20 and the external system So cannot be performed.

The reason for the above is due to reasons as described below. The following describes wireless communication between the console 20 and the access point AP according to the above embodiments. However, the description below is not limited to the console 20 and similar descriptions apply to typical electronic devices which can perform wireless communication.

[Reason 1]

In other words, the console 20 periodically detects the radio wave intensity of the wireless communication between the second wireless communication unit 28 (see FIG. 1A, FIG. 1B and FIG. 2) and the access point AP, and when the detected radio wave intensity I is lower than a set threshold Ith, the search for a new access point AP starts. However, as long as the detected radio wave intensity I is not less than the set threshold level Ith, the search for the new access point AP does not start.

Figure 8:
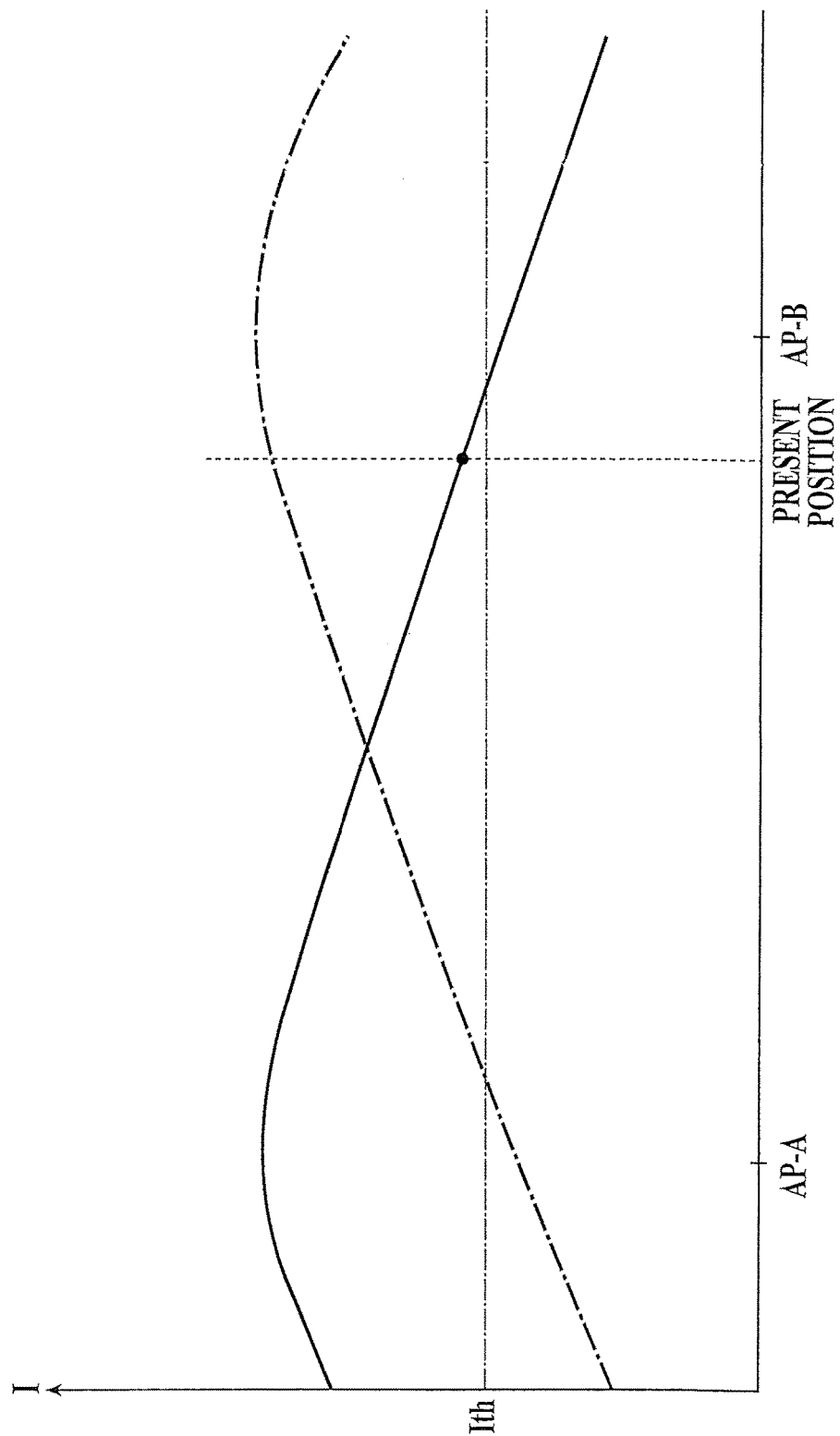
FIG. 8 is a graph showing an example of a relation between radio wave intensity and threshold level of access points AP-A and AP-B in the present position of the console.

Therefore, as shown in FIG. 8, for example, when the console 20 is moved (including carried) from near the access point AP-A to the position to be placed in the access point AP-B, even if the radio wave intensity I of the wireless communication with the access point AP-A decreases and the radio wave intensity I of the wireless communication with the access point AP-B becomes higher, since the radio wave intensity I of the wireless communication with the access point AP-A is not less than the threshold level Ith, the access point AP that communicates wirelessly with the console 20 may not be correctly switched from AP-A to AP-B.

In this case, since the wireless communication is performed between the console 20 and the access point AP-A, the wireless communication between the console 20 and the external system So is not cut. However, since the radio wave intensity I is weak, the communication speed between the console 20 and the access point AP-A becomes late, and for example, the time necessary to transmit the information of the image p for diagnosis from the console 20 to the external system So becomes unusually long.

[Reason 2]

For example, as shown in FIG. 9, when the console 20 is moved from near the access point AP-A to the position to be placed in the access point AP-B, if the radio wave intensity I of the wireless communication with the access point AP-A decreases and becomes lower than the threshold level Ith and the radio wave intensity I of the wireless communication with the access point AP-B is lower than the threshold Ith, the wireless communication between the console 20 and the access points AP-A and AP-B may be cut.

According to the above, when the radio wave intensity I of the wireless communication between the console 20 and all access points AP is below the threshold level Ith, the wireless communication is cut, and the wireless communication between the console 20 and the external system So cannot be performed.

In order to prevent such problems, for example, the following solutions are possible.

[Solution 1]

Until the wireless communication with a new access point AP is created, the wireless communication with the original access point AP is maintained (in other words, not cut).

According to such configuration, it is possible to at least prevent the wireless communication between the console 20 and the access point AP from being cut when the radio wave intensity I of the wireless communication with the access point AP becomes lower than the threshold level Ith while moving the console 20.

[Solution 2]

The threshold level Ith of the radio wave intensity I can be set to be variable.

In other words, when the threshold Ith of the radio wave intensity I, which is to be the reference for the console 20 to switch the access point AP for wireless communication, is set to be variable, for example, as shown in FIG. 8, when the console 20 moves from the position of the access point AP-A toward the access point AP-B, the higher the threshold level Ith is set, the access point AP with which wireless communication is performed can be switched earlier, in other words at a farther position from the access point AP-B (closer to the access point AP-A) without the console 20 coming near the access point AP-B.

As described above, according to a configuration in which the threshold level Ith of the radio wave intensity I can be set to be variable, the access point AP with which the console 20 communicates wirelessly can be switched at a position desired by the radiation technician. With this, it is possible to reliably switch the access point AP with which the console 20 communicates wirelessly.

[Solution 3]

The interval that the radio wave intensity is measured by the console 20 can be changed.

In other words, for example, when the interval of measuring processing to measure the radio wave intensity around the console 20 becomes shorter, it is possible to find a new access point AP with a stronger radio wave intensity I earlier. With this, it is possible to switch to a new access point AP earlier and wireless communication with a stronger radio wave intensity I can be performed. However, when the interval of the measuring processing is made shorter, the amount of energy that is consumed also increases. For example, in a portable console 20 including a battery, the degree of consumption of the battery increases.

Therefore, for example, the interval can be set to a long period in the default state. The interval can be changed to be made shorter when the radiation technician transmits the information of the image p for diagnosis from the console 20 to the external system So. With this, it is possible to suppress consumption of the battery and to transmit the information of the image p for diagnosis to the external system So by wireless communication with a stronger radio wave intensity I.

[Solution 4]

When the access point AP is switched due to the radio wave intensity I of the wireless communication between the console 20 and the access point AP-A becoming lower than the threshold level Ith, there is no meaning in switching the access point AP when the radio wave intensity I of the wireless communication between the new access point AP and the console 20 is weak.

Therefore, for example, a double step threshold level can be employed as the above described threshold level I, and a double step consisting of a high threshold level I th_high and a low threshold level I th_low can be set. When the threshold levels I, I th_high, and I th_low are compared, the result is I th_high>I th_low>I.

For example, when the radio wave intensity I of the wireless communication between the console 20 and the access point AP-A becomes lower than the threshold value I th_low of the low value, the search for the new access point AP starts. When there is an access point AP-B with a radio wave intensity I higher than or equal to the high threshold level I th_high of the high value, the wireless communication is switched to the new access point AP-B, and when the radio wave intensity I of the wireless communication with the new access point AP-B is lower than the high threshold level I th_high, the access point AP is not switched and the wireless communication with the original access point AP-A continues.

According to the above configuration, the following advantages can be obtained. When there is a new access point AP with a stronger radio wave intensity I, it is possible to reliably switch the wireless communication to a new access point AP. When there is no new access point AP with a stronger radio wave intensity I, the wireless communication with the original access point AP can be reliably continued.

The present invention is not limited to the embodiments and configurations as described above, and the embodiments can be suitably modified without leaving the scope of the invention.

The present U.S. patent application claims priority under the Paris Convention of Japanese Patent Application No. 2014-151577 filed on Jul. 25, 2014 the entirety of which is incorporated herein by reference.

What is claimed is:

1. A radiation image capturing method, the method comprising:
    providing a portable radiation image capturing apparatus which can generate image data according to irradiated radiation and transmit the generated image data by wireless communication; and
    providing a portable console including a first wireless communication unit which can receive the image data transmitted from the radiation image capturing apparatus and a second wireless communication unit which can communicate with an external apparatus or system by wireless communication,
    wherein, the console gives priority to the wireless communication through the first wireless communication unit than the wireless communication through the second wireless communication unit.

2. The radiation image capturing method according to claim 1, the method further comprising,
    providing a radiation generating apparatus which irradiates radiation according to operation of an emitting switch,
    wherein, the console prohibits wireless communication through the second wireless communication unit and gives priority to the wireless communication through the first wireless communication unit than the wireless communication through the second wireless communication unit when the emitting switch is operated or a predetermined amount of time passes after the emitting switch is operated.

3. The radiation image capturing method according to claim 1, the method further comprising,
    providing a radiation generating apparatus which irradiates radiation according to operation of an emitting switch; and providing a unit which detects operation of the emitting switch or a unit which detects the emitting switch is operable, wherein, the console prohibits the wireless communication through the second wireless communication unit and gives priority to the wireless communication through the first wireless communication unit than the wireless communication through the second wireless communication unit when the above unit detects operation of the emitting switch or the above unit detects the emitting switch is operable or after a predetermined amount of time passes after either of the above detection.

4. The radiation image capturing method according to claim 1, wherein, the console prohibits the wireless communication through the second wireless communication unit and gives priority to the wireless communication through the first wireless communication unit than the wireless communication through the second wireless communication unit when the capturing order information of the capturing to be performed is selected from obtained capturing order information or a predetermined amount of time passes after the above selection.

5. The radiation image capturing method according to claim 1, wherein, the console prohibits wireless communication through the second wireless communication unit and gives priority to the wireless communication through the first wireless communication unit than the wireless communication through the second wireless communication unit when preview image data or the image data is transmitted from the radiation image capturing apparatus.

6. The radiation image capturing method according to claim 1, wherein, the console prohibits wireless communication through the second wireless communication unit and gives priority to the wireless communication through the first wireless communication unit than the wireless communication through the second wireless communication unit while capturing is performed a plurality of times on one subject; and information of a plurality of images for diagnosis generated based on the image data transmitted from the radiation image capturing apparatus by capturing a plurality of times is transmitted collectively to the external apparatus or system through the second wireless communication unit after the plurality of capturing ends.

7. The radiation image capturing method according to claim 1, wherein, the console prohibits the wireless communication through the second wireless communication unit when the radiation image capturing apparatus is able to perform capturing, and the wireless communication through the second wireless communication unit is allowed only when the radiation image capturing apparatus cannot perform capturing so that the wireless communication through the first wireless communication unit is given priority than the wireless communication through the second wireless communication unit.

* * * * *